United States Patent

Ardito et al.

[11] Patent Number: 5,938,584
[45] Date of Patent: Aug. 17, 1999

[54] CAVERNOUS NERVE STIMULATION DEVICE

[75] Inventors: James R. Ardito, Coon Rapids, Minn.; L. Dean Knoll, Brentwood, Tenn.

[73] Assignee: Cybernetic Medical Systems Corporation, Coon Rapids, Minn.

[21] Appl. No.: 08/970,673

[22] Filed: Nov. 14, 1997

[51] Int. Cl.⁶ .................................................. A61F 5/00
[52] U.S. Cl. ............................................................ 600/38
[58] Field of Search .................................. 607/2, 30, 39, 607/57, 60; 600/38–41

[56] References Cited

U.S. PATENT DOCUMENTS

| | | |
|---|---|---|
| Re. 33,420 | 11/1990 | Sussman et al. ........................... 607/59 |
| 3,941,136 | 3/1976 | Bucalo . |
| 4,542,753 | 9/1985 | Brenman et al. . |
| 4,585,005 | 4/1986 | Lue et al. . |
| 5,117,825 | 6/1992 | Grevious ................................... 607/32 |
| 5,199,430 | 4/1993 | Fang et al. . |
| 5,222,494 | 6/1993 | Baker, Jr. ................................ 607/118 |
| 5,314,453 | 5/1994 | Jeutter . |
| 5,324,315 | 6/1994 | Grevious . |
| 5,370,666 | 12/1994 | Lindberg et al. . |
| 5,433,736 | 7/1995 | Nilsson . |
| 5,454,840 | 10/1995 | Krakovsky et al. . |
| 5,522,865 | 6/1996 | Schulman et al. . |
| 5,562,717 | 10/1996 | Tippey et al. . |
| 5,630,835 | 5/1997 | Brownlee . |

Primary Examiner—Samuel Gilbert
Attorney, Agent, or Firm—Nikolai, Mersereau & Dietz, P.A.

[57] ABSTRACT

An apparatus for treating impotence incorporating a pulse generator and a lead for carrying electrical pulses from the pulse generator to the cavernous nerve. The pulse generator includes a magnetically actuated switching mechanism for extending battery life. One version of the pulse generator is programmable so that the width, frequency and amplitude can be varied.

5 Claims, 4 Drawing Sheets

CAVERNOUS NERVE STIMULATION DEVICE

BACKGROUND OF THE INVENTION

1. Field of the Invention

The present invention relates to the treatment of erectile dysfunction, otherwise known as impotence. More specifically, the present invention relates to either a programmable or non-programmable, implantable device for stimulating the cavernous nerve to cause a penile erection.

2. Description of the Prior Art

High incidences of impotence exist in many segments of the adult male population. Impotence has many causes, some of which are psychological and some of which are physiological in origin. Physiologic impotence can be caused by spinal or other injury, disease, or surgical treatments including prostatectomies, cystectomies, abdominal perineal resections, transurethral resections of the prostate, sphincterotomies, and internal urethrotomies.

Impotence is a significant problem. A plethora of urologists and medical product companies have dedicated substantial time and resources to investigate ways to treat impotence. Many of the treatments developed to date have only been marginally successful. Most do not allow for spontaneous sexual relations. Some require the injection of medication to induce an erection. Others require the attachment of external medical devices such as a mechanical vacuum device. Others require that an internal inflatable device be pumped up. Still others result in the near permanent erection of the penis.

More recently there have been various efforts undertaken to treat impotence using electrical stimulation. For example, U.S. Pat. No. 4,585,005 issued Apr. 29, 1986 to Lue et al describes a device for stimulating a penile erection which includes an electrode coupled to a receiver. The electrode is implanted closely adjacent to the cavernous nerve and intermediate the sacral nerves and apex of the prostate. The receiver is also implanted subcutaneously. The system described in the Lue et al patent also includes an external transmitter coupled to an antenna. When the system is used to induce and maintain an erection, the antenna is placed over the receiver so that the antenna can energize the receiver enabling the receiver to transmit electrical energy to the electrode and to the cavernous nerve. A significant disadvantage of the system disclosed in the Lue et al patent is that the external transmitter and antenna must be held in place during coitus.

Another system for treating impotence through electrical stimulation is disclosed in U.S. Pat. No. 5,454,840 granted on Oct. 3, 1995 to Krakovsky et al. This system includes an implantable, programmable electronic pulse generator coupled to an electrode implanted in proximity to the pelvic splanchnic nerve or the pelvic plexus nerve. The system may also include a storage vessel for storage of a vasoactive drug coupled to a thin tube through which the vacoactive drug is carried to the penis. The system is battery powered and includes an infrared remote control transmitter which is operated by the patient or his partner to control the implanted pulse generator.

Disadvantages also exist with the system described in the Krakovsky patent. First, there is no discussion of any techniques to control power consumption and thereby extend battery life. Second, the use of infrared light to actuate the device limits implantation sites for the device. The penetration of infrared light will, of course, be inhibited by the thickness and density of the epidermis, dermis, and any muscle tissue that separates the infrared transmitter from the receiver components of the implanted device. Third, the system described in Krakovsky stimulates the wrong nerves. Stimulation of these nerves may cause erection if enough energy is delivered. However, such energy would cause other body parts to be stimulated as well, resulting in discomfort. Fourth, the amplitude, frequency and pulse widths described in Krakovsky (FIGS. 12–13) present other issues. The low frequencies indicated (1–2 Hz) will not produce the necessary neuro depolarization to provide a complete erection. The combination of 2.50–5 v amplitude and 0.1 second pulse width, delivers energy at levels which are too great. These can result in unintended muscle contractions, pain, and possible necrosis of the stimulated nerves. All of these problems are addressed and resolved by the present invention.

SUMMARY OF THE INVENTION

To overcome the problems described above, the present invention provides an implantable neurostimulator attached to one or two bipolar electrodes. The bipolar electrodes are intended to be implanted in close proximity to the cavernous nerves of the penis. These two nerves, major and minor, which control the stimulation of penile erection, are derived from the prostatic portion of the pelvic plexus supplying sympathetic and parasympathetic fibers to the helicine arteries and anteriovenous anastamoses of the corpus cavernosam. Direct and appropriate stimulation of these nerves will result in erection without the side effects associated with the stimulation of other nerves to cause erection. To extend battery life and overcome problems associated with the use of infrared light, the implantable device includes a magnetic reed switch that controls an electronic switch between the power source (a lithium battery) and the circuitry which controls and provides for the delivery of electrical stimulating pulses. The switch is activated by simply bringing a magnet into close proximity to the implantable device to open or close the switch. Unlike infrared light, the magnetic lines of force will penetrate body tissues of any density to the distance preset by the strength of the magnet.

In view of the foregoing, it can be seen that an object of the present invention is to provide an apparatus and method for treating male impotence.

A further object of the invention is to treat impotence by stimulating an erection through the application of electrical pulses of a medically effective amplitude, duration and frequency to the cavernous nerves.

Another object of the invention is to provide an implantable programmable pulse generator and electrode for providing such electrical pulses.

Still another object of the invention is to provide a pulse generator which is battery powered and includes means for reducing power drain to extend battery life.

A further object of the invention is to provide a simple, quick, and effective way of actuating the pulse generator which allows for spontaneous sexual relations and does not require that any external device be held in place during such relations.

Other objects and advantages will become better understood by reading the following detailed description of the preferred embodiment in light of the claims, which define the scope of the invention, and the drawings.

DETAILED DESCRIPTION OF THE PREFERRED EMBODIMENT

Figure 1:
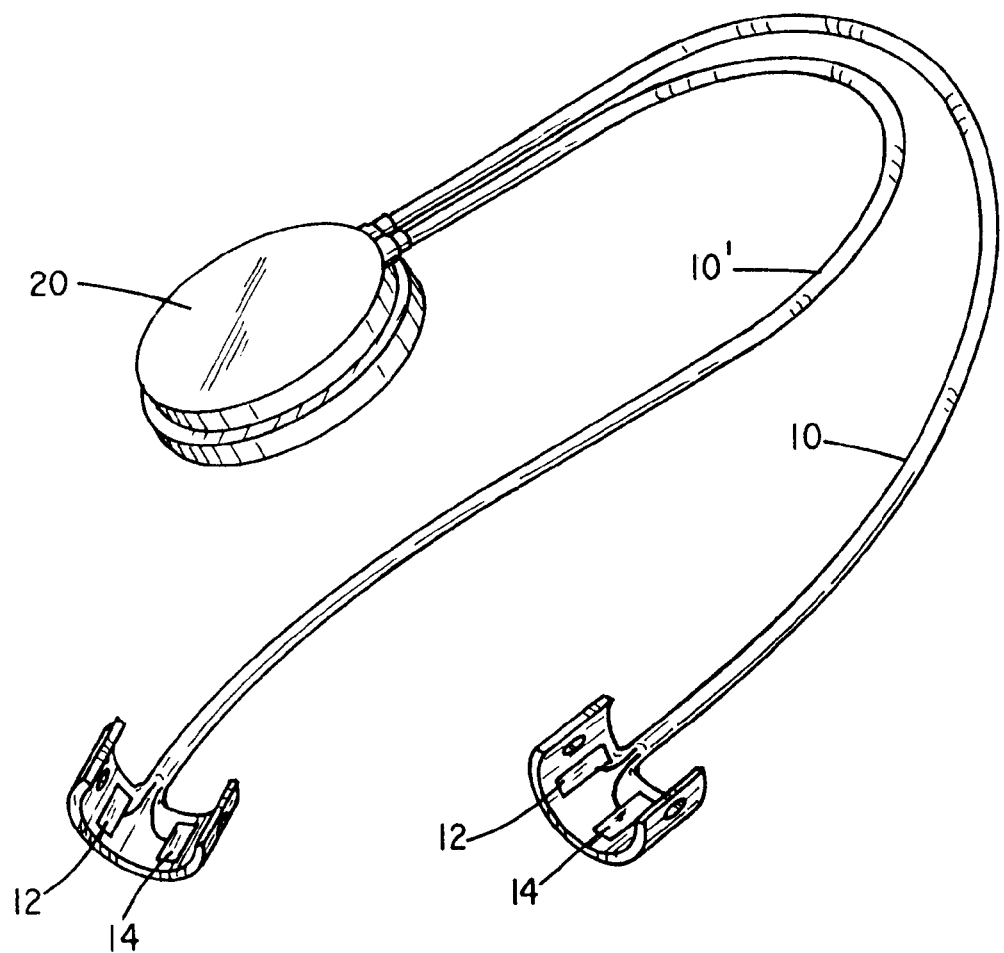
FIG. 1 is a perspective view showing the exterior of the pulse generator and bipolar leads attached thereto.
Figure 2:
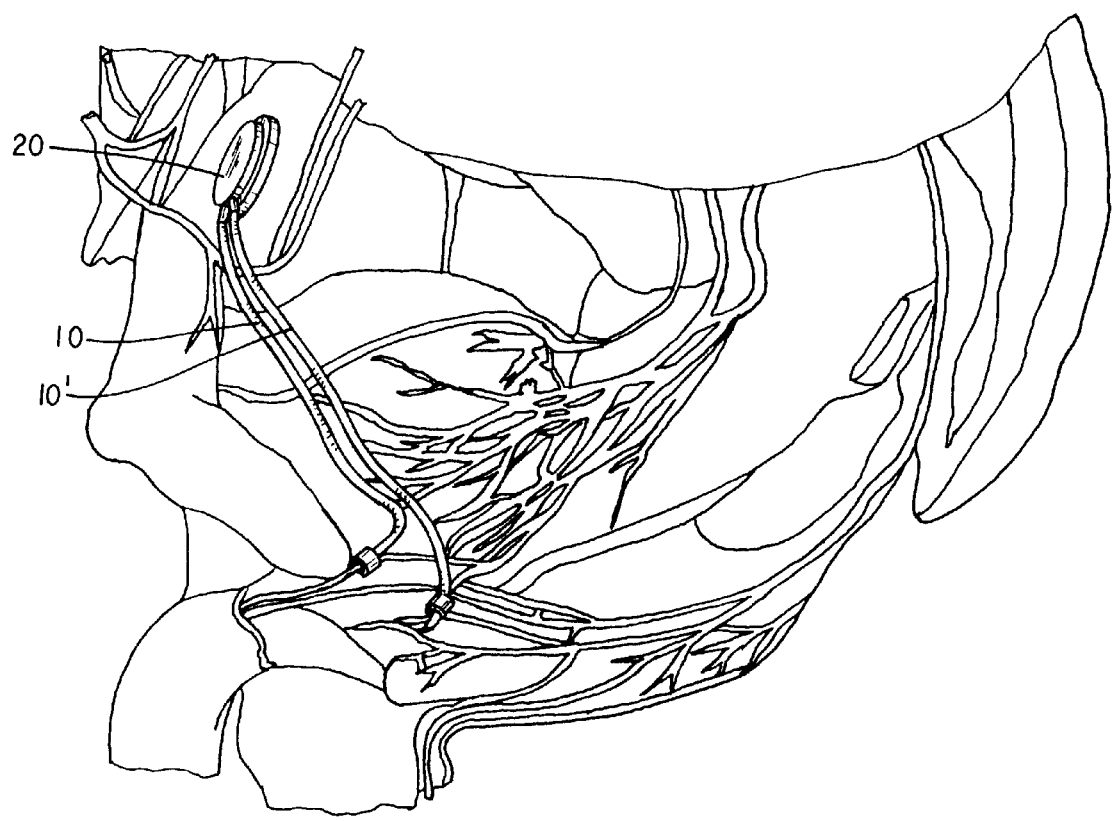
FIG. 2 is a view showing the preferred implementation site for the electrodes of the bipolar lead.

FIG. 1 shows the implantable cavernous nerve stimulator of the present invention. As shown, the nerve stimulator includes two bipolar leads 10 and 10' each having a first electrode 12 and a second electrode 14. As shown in FIG. 2, one each bipolar lead couples a pulse generator 20 to the greater and lesser cavernous nerves.

Figure 3:
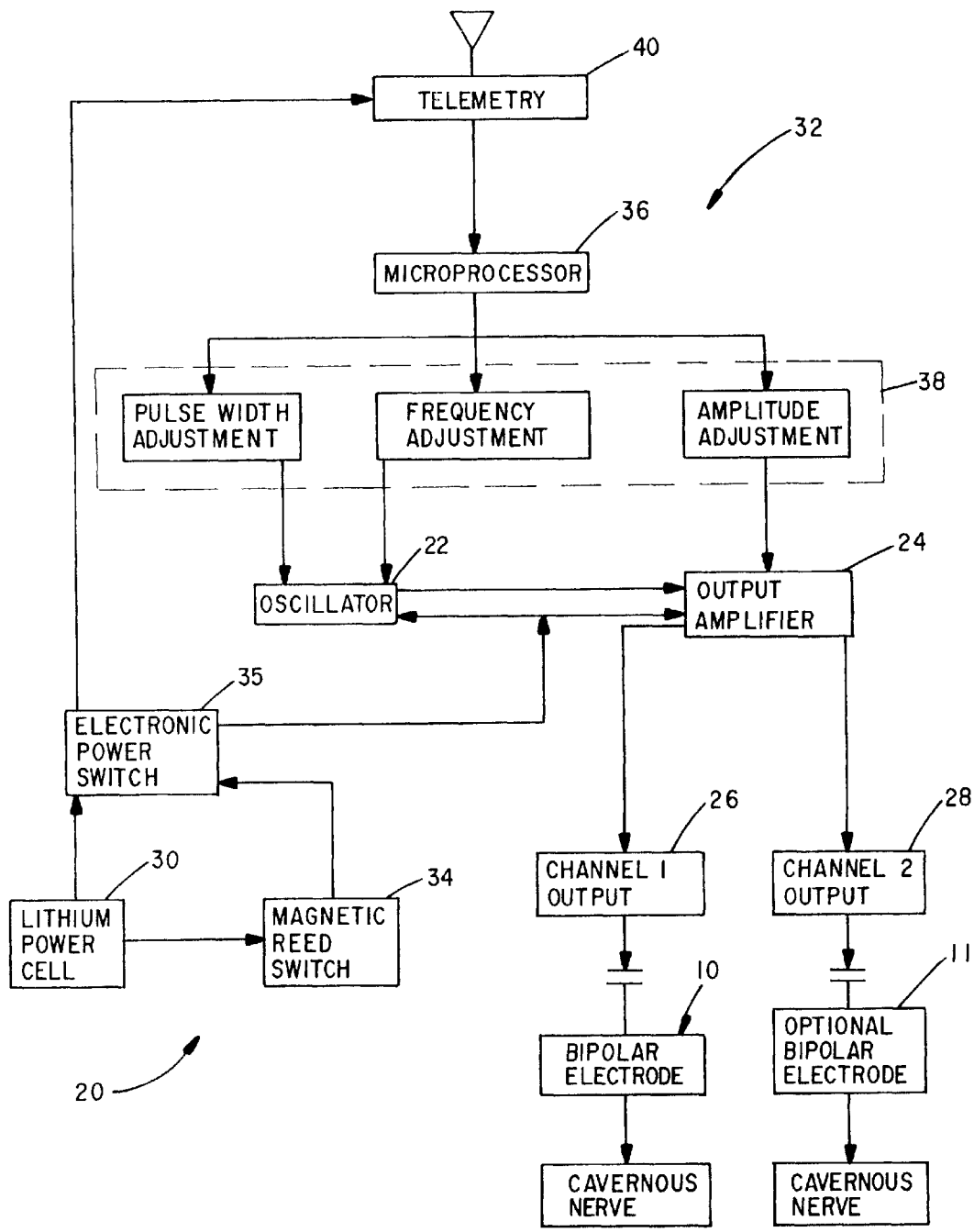
FIG. 3 is a block diagram of a programmable version of the pulse generator.
Figure 4:
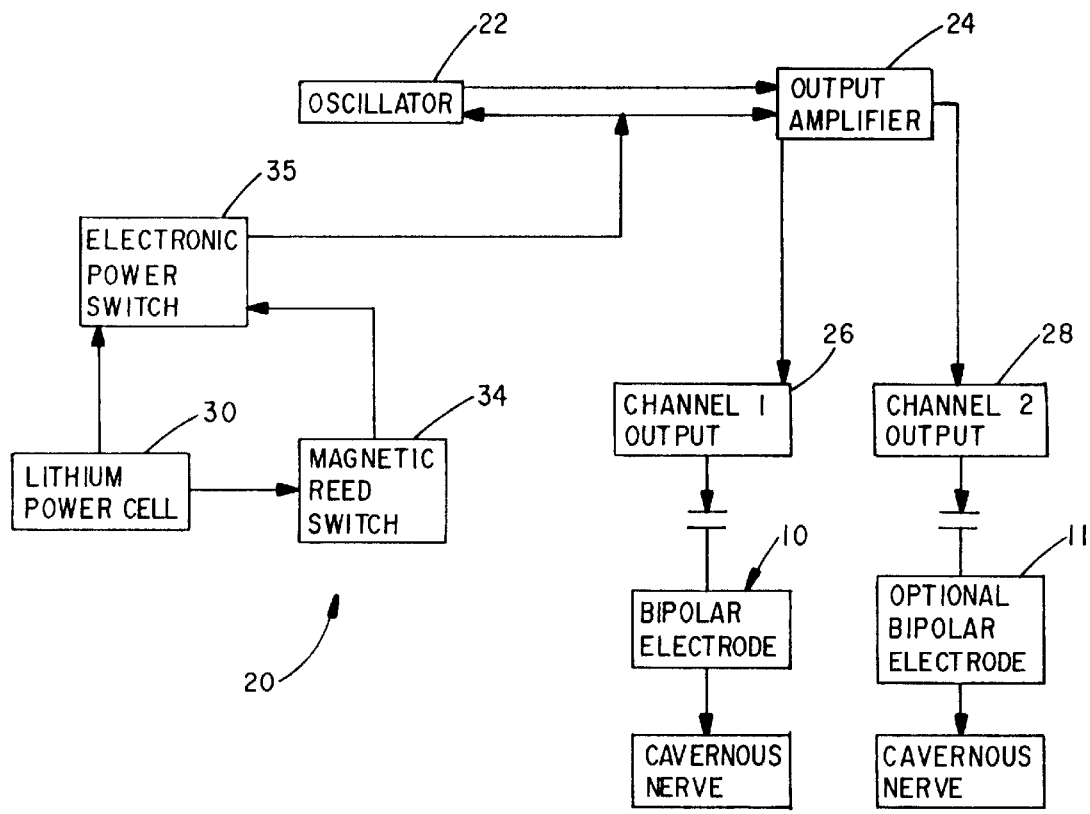
FIG. 4 is a block diagram of a non-programmable version of the pulse generator.

FIGS. 3 and 4 show two versions of the pulse generator 20. In each version, the pulse generator 20 includes an oscillator 22, an output amplifier 24, a first output channel 26 and a second output channel 28. The first output channel 26 generates electrical pulses which are delivered to the major cavernous nerves via the electrodes of the bipolar lead 10. The second output channel 28 is optional. An optional bipolar lead 10' can be connected to output channel 28 to deliver pulses to the minor cavernous nerves. Each version of the pulse generator also has a battery 30, which is preferably a lithium-iodide power cell, a switching station consisting of a magnetic reed switch 34, and an electronic power switch 35. The programmable version of the pulse generator 20 shown in FIG. 3 also has programmable control circuitry 32. The programmable control circuitry 32 includes a microprocessor 36 which controls the operation of the pulse generator in accordance with a programmed set of instructions stored in the microprocessor's read only memory (ROM), random access memory (RAM) 38 and telemetry link 40 for exchanging programming signals with an external source. The switching station may, alternatively, consist of a polarized magnetic reed switch.

In addition to the nerve stimulator itself, the programmable system for treating impotency also includes an external programmer for delivering program parameters to the telemetry link 40 and an external magnet for actuating the magnetic reed switch 34. Neither the magnet nor the external programmer are shown. The external programmer is of the type typically used to program implantable medical devices, such as heart pacemakers. Such programmers typically transmit RF signals for programming, although a programmer which transmits magnetic signals might also be used.

The battery 30 is designed to perform several functions. In both, the version shown in FIG. 3 and the version shown in FIG. 4, the battery 30 supplies the oscillator 22 with the energy required to deliver electrical pulses to the cavernous nerves. In both versions, it also provides a continuous low voltage to the electronic power switch 35. In the version shown in FIG. 3, the battery 30 can also supply a continuous low voltage to the memory 38 to preserve programmed parameters stored therein. This function, however, is not required if the memory 38 is of the type that can store data for extended periods of time even when not powered. Examples of such memory include flash memory, electrically alterable read only memory, and electrically programmable read only memory. Finally, the battery 30 supplies power to the microprocessor 36 and telemetry link 40 of the version shown in FIG. 3 for control purposes.

An important consideration is the life of the battery 30. Whenever the battery 30 dies, a surgical procedure is required to replace the pulse generator. Thus, it is important that the life of battery 30 be extended however it is reasonably possible to do so. The life of battery 30 is extended in the present invention by substantially reducing power drain when the pulse generator is not being used to stimulate an erection. This is accomplished in both versions by placing the magnetic reed switch 34 and electronic power switch 35 between the battery 30 and the oscillator 22. In the version shown in FIG. 3, the switches 34 and 35 are also located between the battery 30 and the telemetry 40, the microprocessor 36 and the memory 38.

Electronic power switch 35 is an electrically actuated bistable switch having an open position and a closed position. The power switch 35 is triggered by a magnetic reed switch 34. When the switch 35 is open, no power is delivered from the battery 30 to the telemetry link 40, microprocessor 36 or oscillator 22. Thus, there is no current drain through these components when the switch 35 is open. When the switch 35 is closed, power is provided from the battery 30 to these components to deliver pulses in a controlled manner through the electrodes to the major and minor cavernous nerves. As indicated above, the switch 35 is opened or closed by introducing an external magnet into close proximity with the magnetic reed switch 34. The switching circuit 35 will remain open or closed until the magnet is reintroduced.

Using a microprocessor 36, as contemplated by the version shown in FIG. 3, to control the delivery of stimulation pulses has certain advantages. One advantage is that the delivery of pulses is under program control. Another is that the program parameters can be altered to change the performance of the pulse generator 20. For example, the pulse generator can be reprogrammed to alter pulse width, pulse frequency, or pulse amplitude. The telemetry link 40 is used to communicate with an external programer to check or alter the program parameters.

In view of the foregoing description, implantation and use of the nerve stimulator will now be described. First, the pulse generator 20 will be implanted subcutaneously alongside the symphysis pubis (pubic bone). The silicone coated platinum wires leading to the electrodes 12 and 14 of the bipolar lead 10' are run subcutaneously to the area of the penis base where they are sutured in proximate contact with the cavernous nerves. To accomplish this, an incision is made just superior to the base of the penis and the cavernous nerves are isolated. An external pulse generator is then attached to the lead. The external pulse generator is used to perform tests to verify proper electrode placement and satisfactory patient response to stimulation. The external pulse generator is then detached from the lead 10 and the electrodes 12 and 14 of the lead 10 are attached to the output channel 26 of the implantable pulse generator 20. The second, optional lead 10' can also be implanted, tested and ultimately attached to the second output channel 28 if desired.

If a non-programmable pulse generator is used, one designed to deliver pulses having the appropriate width, frequency and amplitude is selected. All incisions are then closed and the patient is allowed to heal.

If a programmable pulse generator like that shown in FIG. 3 is implanted, after about a four week healing time the patient returns to the surgeon's office where final programming of the implantable pulse generator 20 takes place. As indicated above, this programming is performed using an external radio frequency transmitter that emits coded signals that sets the parameters to be used by the pulse generator 20. Whether the non-programmable version of the pulse generator is used, it is important that the pulse characteristics be such that their application to the cavernous nerves will stimulate an erection without causing undue pain, discomfort, nerve damage or tissue damage. Preferably the pulses will have a frequency of 60 Hz, an amplitude of 3.5 volts and a width of 300 microseconds. When the programmable version is used, these parameters are programmable within a range of approximately plus or minus 15% of these values.

One benefit of the present invention is that the patient should retain all sensation and responses exhibited prior to implantation. When the patient wishes to produce or augment an erection, the external magnet is placed momentarily over the pulse generator 20 to actuate the reed switch 34 and the electronic power switch 35 thus triggering the preprogrammed or preset stimulation protocol to transmit electrical stimulation pulses to the cavernous nerves. When intercourse is complete, the magnet is again momentarily placed over the pulse generator 20 to actuate the switches 34 and 35 so that stimulation pulses are terminated so that the erection can normally fade.

The present invention may be embodied in other specific forms without departing from its spirit and the foregoing description is not intended to be limiting. Accordingly, reference should be made to the claims which define the scope of the invention.

What is claimed is:

1. An apparatus for treating patients for impotency comprising:

a. an implantable pulse generator, said pulse generator including an oscillator and output amplifier, and at least one output channel for producing pulses of a desired width frequency and amplitude;

b. a battery, and a switching station connected in circuit with the battery and actuatable by an external magnet between (i) a first state in which no power is supplied to the oscillator and output amplifier, and (ii) a second state in which power is supplied to the oscillator and output amplifier of the pulse generator, said switching station including an electronic power switch which is triggered by a magnetic reed switch; and c. an implantable elongated bipolar lead having electrodes for delivering stimulating pulses of proper width, frequency and amplitude from the output amplifier of the pulse generator to the cavernous nerves of the patient.

2. The apparatus of claim 1 wherein said switching station includes a polarized magnetic reed switch.

3. The apparatus of claim 1 wherein said apparatus includes a second output channel and a second implantable elongated bipolar lead having electrodes for delivering stimulating pulses of proper width, frequency and amplitude from the output amplifier of the pulse generator to the cavernous nerves of the patient.

4. The apparatus of claim 1 further including a programmable microprocessor-based controller coupled to the pulse generator so that the width, frequency and amplitude of the pulses produced by the pulse generator can be adjusted.

5. The apparatus of claim 1 wherein said microprocessor-based controller also includes telemetry means for receiving programming signals from an external programmer.

* * * * *